United States Patent [19]

Daudt et al.

[11] 4,377,675

[45] Mar. 22, 1983

[54] AMORPHOUS MATERIALS DERIVED FROM AQUEOUS METAL AMMINE SILICONATE SOLUTIONS

[75] Inventors: William H. Daudt; Cecil L. Frye, both of Midland, Mich.; James F. Hyde, Marco Island, Fla.

[73] Assignee: Dow Corning Corporation, Midland, Mich.

[21] Appl. No.: 277,786

[22] Filed: Jun. 26, 1981

Related U.S. Application Data

[62] Division of Ser. No. 78,415, Sep. 24, 1979.

[51] Int. Cl.$^3$ .................................................. C08G 77/04
[52] U.S. Cl. ........................................ 528/25; 528/28; 528/30; 528/33; 525/102; 106/193 R; 106/197 R; 106/287.26
[58] Field of Search ................ 260/429 R, 429.9, 430, 260/438.1, 431; 528/25, 28, 30, 33; 106/193, 197, 287.26; 525/102

[56] References Cited

U.S. PATENT DOCUMENTS

| | | | |
|---|---|---|---|
| 3,692,865 | 9/1972 | Lengick | 528/30 X |
| 3,705,120 | 12/1972 | Kawaguchi | 528/29 |
| 3,714,119 | 1/1973 | Marks et al. | 528/30 X |
| 3,886,226 | 5/1975 | Asai et al. | 528/29 X |
| 3,941,856 | 3/1976 | Creasey et al. | 528/33 X |
| 4,008,198 | 2/1977 | Krohberger et al. | 528/33 X |
| 4,064,154 | 12/1977 | Chandio et al. | 528/28 X |
| 4,075,154 | 2/1978 | Itoh et al. | 528/33 X |
| 4,098,840 | 7/1978 | Yoshida et al. | 525/102 |
| 4,222,917 | 9/1980 | Razzano et al. | 528/29 X |
| 4,277,525 | 7/1981 | Nakayama et al. | 106/197 R |

OTHER PUBLICATIONS

Borisov et al., Organosilicon Heteropolymers and Heterocompounds, Plenum Press, N.Y., pp. 109, 121, 124, 125, 135, 136, 138 to 140, 147, 166, 293, 324, 328, 329, 359, 385, 386, 411 to 413, 439, 440, 448, 449 to 451, 456, 457, 464, 477, 487, 488 and 492 (1970).

*Primary Examiner*—Helen M. S. Sneed
*Attorney, Agent, or Firm*—Robert L. McKellar

[57] ABSTRACT

Aqueous metal ammine siliconate solutions are the reaction products of selected metals or metal derivatives, selected mono-organosilicon materials, certain alkaline nitrogen compounds having the formula R—NH$_2$, and water. Amorphous materials are formed when volatiles are removed from the siliconate solutions. The metal components in the resulting amorphous materials are not readily leached out by normal weathering, washing or the like. The solutions are useful in a method for treating substrates, such as wood, textiles, thread, canvas, carpeting, paper and masonry, to confer antimicrobial properties. The organosilicon component can be selected so that such treatments also confer either hydrophobic or hydrophilic properties to the substrates. The components of the solutions can be selected to enhance their ability to form continuous films of amorphous materials when used in such treatments, making the solutions useful to provide antimicrobial coatings which may be either hydrophobic or hydrophilic. Such amorphous coatings are useful for applications such as wood preservation, masonry water repellents, marine varnishes and as treating agents to give a desirable hand to fabrics. Powdered amorphous materials can be used to produce antimicrobial ointments. The solutions are useful as hardeners for water-reducible resins and emulsions, including latex paints. The solutions can also be adapted to include components which may be slowly leachable from the resulting amorphous materials which can thus serve as controlled-release binders to provide prolonged antimicrobial protection not only to the treated surfaces but also to their immediate surroundings.

9 Claims, No Drawings

AMORPHOUS MATERIALS DERIVED FROM AQUEOUS METAL AMMINE SILICONATE SOLUTIONS

This application is a division of application Ser. No. 78,415, filed 9/24/79.

BACKGROUND OF THE INVENTION

1. Field of the Invention

This invention relates generally to the field of aqueous metal siliconate solutions and amorphous materials derived therefrom, and to uses thereof, including both the treatment of various substrates and the modification of water-reducible protective coating systems.

2. Description of the Prior Art

Certain metals and metal compounds have long been known for their antimicrobial nature. Copper and zinc oxide are two such materials. For example, zinc oxide has been used as a primary ingredient in ointments and salves. Zinc oxide has been found to be environmentally and toxicologically unobjectionable, and it is inexpensive.

Attempts have been made to dissolve useful amounts of compounds of metals such as copper and zinc in ammoniacal solutions; however, the readily available oxides of zinc and copper are relatively poorly soluble even in aqueous ammonia. The most successful such efforts have been by adding the metal oxides to aqueous ammonia containing acidic ammonium salts such as ammonium carbonate or ammonium thiocynate (U.S. Pat. No. 3,945,834). In this way the metal oxide is converted to a water soluble salt of the acid wherein the metal cation is coordinated with several ammonia molecules. Although the solubility of zinc oxide or basic cupric carbonate in aqueous ammonia is greatly enhanced by the presence of such acidic salts, their use has the attendant disadvantage of introducing large amounts of leachable non-functional salts to treated objects. For instance, wood impregnated with such solutions would contain large quantities of leachable ammonium carbonate, ammonium thiocyanate, etc. Furthermore, the metal salts themselves may tend to be too easily leachable for optimum long term protection.

Such metal salts are sometimes too easily redissolved and removed from the treated material during rains or washing. The use of too readily leachable complexes containing metals, such as copper, known to be offensive in high concentrations to living things, is environmentally undesirable. Indeed, such complexes may be quite poisonous when they are too readily leached into the surrounding terrain during normal weathering.

Furthermore, such metal salts do not impart a hydrophobic nature to materials which have absorbed them. Since water repellency is a desirable characteristic which aids in the preservation of cellulosic fibers and masonry, materials which provide hydrophobicity in addition to antimicrobial properties are desirable.

Although alkali metal and alkaline earth metal organosiliconates are described in the patent literature (U.S. Pat. Nos. 2,507,200 and 2,438,055) and in the scientific literature [C. G. Ladenburg, Ann. 173, p. 148; Meads and Kipping, J. Chem. Soc. 105, p. 679; and Kather and Torkelson, Ind. and Eng. Chem. 46(2), p. 381 (1954)], none of these disclosures teaches the use of ammonia to stabilize siliconate salts of metals. These materials have the serious disadvantage of leaving water soluble alkali metal or alkaline earth metal salts in treated objects, the presence of which can adversely affect the hydrophobicity otherwise obtainable by the organosilicon resin deposit.

The preparation of various metalorganosiloxanes by the reaction of the sodium salts of organosilanetriols with metal chlorides in organic solvents is disclosed by A. A. Zhdanov, K. A. Andrianov and M. M. Levitskii in the U.S.S.R. publication Seriya Khunicheskaya, No. 2, pp. 395–399, February, 1976. The compounds, which are made by a relatively tedious and complicated procedure, so disclosed are of low molecular weight and are soluble in organic solvents.

SUMMARY OF THE INVENTION

It is a primary object of this invention to overcome the disadvantages of the prior art.

It is another object of this invention to present as a useful new composition of matter an ammonia-stabilized metal siliconate solution.

It is also an object of this invention to present as a new composition of matter a hydrolytically stable, insoluble, high-molecular-weight copolymeric amorphous material having metal-oxygen and silicon-oxygen structural units.

It is still another object of this invention to treat absorbent substrates, such as cellulosics and masonry, for protection against microbial attack.

It is also an object of this invention to avoid environmental damage by an antimicrobial agent.

It is a further object of this invention to impart hydrophobic properties to porous or absorbent substrates such as cellulose, masonry, etc.

It is yet an additional object of the invention to produce an ointment suitable for use in antimicrobial treatment.

It is an object of this invention to treat substrates with amorphous coatings which may be either hydrophilic or hydrophobic.

It is a further object of this invention to modify the hand of synthetic fabrics and to prevent static build-up.

It is still another object of this invention to protect surfaces from weathering and from marine fouling.

It is also an object of this invention to harden coatings such as those obtained from water-reducible paints which contain alkyds, acrylic emulsions, water soluble cellulose derivatives such as hydroxyalkyl cellulose resins, mixtures thereof and the like.

These and other objects are accomplished by an aqueous metal siliconate solution which comprises, generally speaking, the reaction product of metals, metal compounds or mixtures thereof which yield metal ammine cations in the presence of $RNH_2$; $R—NH_2$; a hydrolyzable mono-organosilicon material; and water.

R can be H, alkyls of up to 3 carbon atoms, aminoalkyls of 2–6 carbon atoms, or mixtures thereof. The $—NH_2$ molar concentration is equal to at least n times the molar concentration of the metal where n is the coordination number of the metal.

The mono-organosilicon material is one which undergoes hydrolysis in the presence of the other reactants to yield mono-organosilanols or siloxanols and other hydrolysis products which are not more acidic than the silanols or siloxanols. The organo moiety in the mono-organosilicon material may contain up to about 50 carbon atoms and is selected from the group consisting of saturated and unsaturated hydrocarbons having from 1 to about 6 carbon atoms, halohydrocarbons having up to 6 carbon atoms and wherein the halo substitution is at a location other than at the alpha or beta location, aminohydrocarbons, radicals containing one or more ether or thioether linkages, hydroxyfunctional alkyl radicals, carbomethoxyalkyl radicals, carbamoylaklyl radicals, quaternary ammonium or phosphonium bearing alkyl radicals and mixtures thereof. The methyl radical is a preferred hydrophobic organo substituent because of the low cost and ready availability of suitable methyl-silicon containing materials such as MeSi(OMe)$_3$. The silicon material is present in an amount sufficient to yield a silicon/metal ratio of from about 1 to about 10.

The water should be present in an amount sufficient to achieve an aqueous metal siliconate solution; that is, water should be the component which is present in excess. It is preferred that the weight of the water present in the solution be at least substantially equal to the weight of the R—NH$_2$ material present.

In another aspect the invention comprises an amorphous material which is the resultant product upon evaporation of water, alcohols and volatile nitrogen bases from the aqueous siliconate solution. The organosilicon material can be selected to give the amorphous material hydrophilic or hydrophobic properties. The organosilicon material, the silicon/metal ratio and R—NH$_2$ can also be selected to enhance the film-forming properties of the amorphous material.

In another aspect, the invention comprises a method for treating a substrate by applying to the substrate an aqueous metal ammine siliconate solution of the present invention and allowing the volatiles to evaporate from the solution. Although the substrate can be absorbing or non-absorbing, good results are more generally obtained with the former.

In another aspect the amorphous material is combined with a carrier to form a blend, such as a medicinal ointment, a lubricating grease or a filled synthetic rubber.

In yet another aspect, a water-reducible material, such as a latex paint vehicle, can include the aqueous siliconate solution which performs as a hardener and confers antimicrobial properties to the material.

DETAILED DESCRIPTION

Throughout the following description, temperatures are given in Celsius. Me, Vi, Ph and Et are sometimes used to indicate methyl, vinyl, phenyl and ethyl, respectively. Ratios are molar unless otherwise indicated, and percentages are by weight. For example, the ratios of concentrations of a solution containing MeSi(OMe)$_3$, ZnO and NH$_3$ may often be described as Si/Zn, N/Zn or Si/N/Zn ratios.

Any metals or metal derivatives of substances which are not more acidic than the silanols or siloxanols (described below) and which dissolve in the reaction mixture to yield metal ammine cations in the presence of RNH$_2$ may be used. The oxides or hydroxides of metals in groups I B and II B of the Periodic Table of the Elements are the preferred materials for use in this invention.

Silver oxide, basic copper carbonates (e.g. malachite, azurite, and chessylite), cadmium oxide, zinc oxide, mercuric oxide and mixtures thereof have been found to provide good results in the composition and method of this invention. Thus it can be seen that the metal oxides and hydroxides useful in this invention can be pure compounds or the substantially cheaper commercially available versions. Zinc oxide is often preferred because of its availability, low cost and ecological acceptability.

Any compound of the formula R—NH$_2$ where R is H, methyl, ethylpropyl, isopropyl, or an aminoalkyl with 2–6 carbon atoms, as well as mixtures thereof may be used. However, ammonia is preferred because of its relatively low cost and availability.

R—NH$_2$ can be present in any useful amount. However, the —NH$_2$ molar concentration should be present in an amount equal to at least the coordination number of the metal. That is, if the coordination number of the metal is 4, —NH$_2$ should be present in a molar concentration of at least four times the molar concentration of the metal. —NH$_2$/metal molar ratios lower than the coordination number of the metal prevents complete reaction of the oxide or hydroxide, which tends to permit undesirable organosilsesquioxane gel formation.

The N/metal molar ratio is often maintained higher than the coordination number so that the reaction proceeds more rapidly.

Suitable silicon materials for use in the present invention are any mono-organosilicon materials which can undergo hydrolysis to yield silanols or siloxanols. Those which yield by-products that are not more acidic than the silanols or siloxanols are preferred. Mono-organosilicon materials are defined, for the purposes of this description, as silicon products having one Si—C bond. The use of silicon materials which form more acidic by-products upon hydrolysis often results in the undesirable formation of silsesquioxane gels, or requires the presence of additional metal oxide to compensate for that which is consumed by the too acidic by-product. In such cases the acidic by-products neutralizes the metallic base which is needed to maintain the organosilicon moieties in the form of soluble low molecular weight anionic species. If by-products of such greater acidity result, then it is necessary to use additional metal oxide and R—NH$_2$ to assure that enough is present to not only neutralize the by-products but also to stabilize the acidic silanols in their anionic form.

Silicon materials with no Si—C bonds do not yield useful solutions with metals even in the presence of R—NH$_2$ (such as aqueous ammonia). Such solutions are observed to precipitate insoluble metal silicates and silica. Silicon materials with more than one Si—C bond will dissolve metal oxides in aqueous ammonia, but such siloxanolate salts tend to disproportionate or decompose to form siloxanes which form a water insoluble phase, leaving the metal hydroxide in aqueous ammonia, which may then form some insoluble metal oxide precipitate.

The mono-organosilicon material must be hydrolyzable to silanols under the alkaline conditions employed. Thus, in addition to the organo substituent on the silicon atom, the mono-organosilicon material normally contains three hydrolyzable moieties attached to the silicon atom. Upon hydrolysis these hydrolyzable moieties should preferably not yield by-products which are more acidic than the silanol groups formed for reasons given above. Specific examples of hydrolyzable moieties which can be present in the mono-organosilicon materials useful in this invention are methoxy, ethyoxy, $\beta$-methoxyethoxy, amino and alkylamino-groups as well as hydrogen and siloxane oxygen. The methoxy group is the preferred hydrolyzable moiety at this time. Disilanes such as

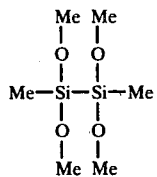

can also be used, however, they are not preferred because of their expense and the undesirable hazard of $H_2$ production resulting from their hydrolysis. For similar reasons $MeHSi(OMe)_2$ is not preferred.

Organotrialkoxysilanes are the preferred mono-organosilicon materials for use in the practice of this invention. Because of its low cost and ready availability, $MeSi(OMe)_3$ is the most preferred mono-organosilane. Other mono-organosilanes useful in this invention include: $MeSi(OEt)_3, PhSi(OMe)_3$, $ViSi(OMe)_3$, $F_3CCH_2CH_2Si(OMe)_3$, $MeOOC(CH_2)_{10}Si(OMe)_3$,N-α-(trimethoxysilyl)ethylpyrrolidone, dimethyl-n-octadecyl[3(trimethoxysilyl)propyl]ammonium chloride, (3-hydroxypropyl)trimethoxysilane, $MeO(CH_2CH_2O)_nCH_2CH_2CH_2Si(OMe)_3$ where n=0–20, tributyl(3-trimethoxysilylpropyl)phosphonium chloride, 3-aminopropyltrimethoxysilane, N-[3-trimethoxysilylpropyl]-ethylenediamine, and 10(carbamoyldecyl)-trimethoxysilane.

Useful amounts of the silicon material are those which provide stable siliconate solutions. Instability occurs at different Si/metal ratios in different systems depending largely on the organo-substituent on the silicon and also on the relative concentrations of the various components. For example, when the monoorgano-silicon-material is $MeSi(OMe)_3$, the Si/metal upper limit is about 3.6. With other substituents, the upper stability limit can be higher. In unstable solutions some of the siloxanols condense to gels.

Solutions having silicon/metal ratios of about 1.0 or greater are frequently used. At ratios below about 2.0, it becomes increasingly difficult to get the metal compound into solution when the metal is in Group II B.

Silicon material concentrations which provide silicon/metal ratios of above 2.0 are sometimes preferred because this results in metal oxides going into solution at relatively high rates.

It is believed the combination of water, R—$NH_2$, metal oxide and mono-organosilicon material form an aqueous metal ammine siliconate which is a nitrogen-complexed metal salt. This belief and the chemical reactions described herein are based on the best information presently available and not intended to be limiting in any way with regard to the invention as delineated elsewhere herein by examples and specific claims.

For example, when methyltrimethoxysilane is hydrolyzed with aqueous ammonia in the presence of powdered zinc oxide, the following reactions are believed to take place: First, the alkoxysilane hydrolyzes to yield siloxanols such as I.

 (I)

In the presence of aqueous ammonia, I reacts with ZnO to form the low molecular weight siliconate salt, II, as follows:

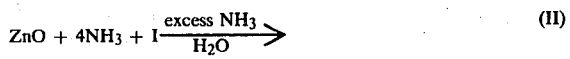 (II)

It is believed that the metal ammine hydroxide is sufficiently alkaline to actually bring about hydrolysis of any initially formed siloxane condensates, thereby returning them to a lower molecular weight form. In some instances transient gelation has actually been observed, followed by re-dissolution to yield a low viscosity aqueous solution.

Ordinarily, however, the hydrolyzate (I) does not gel because it reacts to form the salt (II) sufficiently rapidly that polycondensation is avoided. In comparable tests under similar conditions where the metal oxide or hydroxide is not present, the hydrolyzates in 28% aqueous ammonia condense within minutes to gels. Metal oxides such as ZnO or CuO alone dissolve only sparingly in aqueous ammonia itself. Thus, although neither aqueous ammonia nor metal oxide is sufficiently alkaline to maintain a stable silanolate solution when used individually, the use of both leads to the formation of a metal ammine hydroxide base which is sufficiently alkaline to form a stable siliconate salt.

The hydrolyzable silanes normally produce by-products in the reaction (described above) by which the solutions of the present invention are made. For example, $MeSi(OMe)_3$ will yield MeOH in such a reaction. Such reaction by-products help to keep the siliconates in solution in commercially useful amounts. In the $MeSi(OMe)_3/ZnO/NH_4OH$ system the reaction by-produced alcohol helps to keep the siliconate in solution in useful amounts up to a Si/metal ratio of about 3.6. Other siliconates exhibit higher Si/metal ratios before the reaction by-product solvent becomes unable to keep a commercially useful amount of siliconate in solution.

Miscible solvents may also be added to the reaction system in amounts up to about 50% by weight to make higher Si/metal ratios commercially useful. Such solvents may also be used to maintain homogenity when the organosilicon material contains hydrophobic organic groups with more than 2 carbon atoms and to aid in blending the solution with organic resins. Typically useful solvents are low molecular weight alcohols or alkoxy-alcohols having from 1 to about 6 carbon atoms. Examples of such solvents are isopropyl alcohol, n-butyl alcohol, methanol and ethylene glycol monobutyl ether.

If desired, the solution may also contain various conventional additives which are dispersible and stable in the system, including such materials as dyes, colloids, surfactants, other water thinnable polymers, soluble metal salts, quaternary ammonium salts and mixtures thereof. For example, dyes can be added whenever a particular color is desired. In some instances, a metal salt or a quaternary ammonium salt can be added to produce an amorphous material with tailored or controlled leachability. Because of their known antimicrobial nature, quaternary ammonium salts are sometimes added when it is desirable to supplement the antimicrobial nature of the amorphous material obtained upon removal of volatiles from the solutions of this invention (as described below).

The ammonia-stabilized metal siliconate solutions can be converted into amorphous materials by removing the volatile nitrogen-containing bases. It is observed by microscopic examination and X-ray diffraction techniques that the material is amorphous and devoid of crystalline structures, i.e., the metal oxide is present in a combined state and is no longer present as a discrete phase. It is thought the solubilized siliconate salt condenses to a copolymer incorporating the metal oxide units as the volatiles leave. Thus, the water soluble ionic metal ammine siliconate salt is converted to an insoluble covalent copolymer containing metal-oxygen-silicon bonds upon loss of ammonia or other volatile bases and water. For instance, in the case of the ammoniated zinc methylsiliconate described above, this reaction product is represented by formula (III).

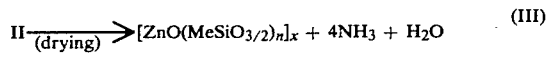  (III)

The material having the general formula III is normally formed by drying the siliconate solution. Such drying is typically accomplished by simple air drying under ambient conditions, but, if desired, may be assisted by evacuation and/or the application of heat. Although the amorphous copolymer can be redissolved by reaction with aqueous ammonia, it is insoluble in water and common solvents, further attesting to its probable covalent cross-linked structure. When the Si/metal ratio is higher it may be desirable to use alcoholic aqueous ammonia to completely redissolve the amorphous materials. Alcoholic solutions are useful at different Si/metal ratios in different embodiments.

Some of the formulations, although useful as protective impregnants, yield films which wrinkle and craze during the drying process. The components of the solution can be selected to enhance the ability of the solution to form a coherent film of the amorphous material. The film integrity often can be enhanced by increasing the Si/metal ratio. The film-forming ability can also be enhanced by the use of a mono-organosilicon material wherein the organo substituent has a relatively long carbon chain. The film-forming ability is observed to be improved when the organo substituent on the silicon contains more than about two carbon atoms.

The film-forming ability of the solution can also be enhanced by the use of a water dispersible plasticizer. Low molecular weight polyglycols (i.e., those having from 1 to 15 ethylene oxide units) are typical of materials which make useful plasticizers, although any suitable material can be used. Other examples of suitable materials are sorbitol, polyvinylalcohols with molecular weights of less than about 10,000 or hydroxyalkylcellulose resins.

The organo substituent of the mono-organosilicon material can be selected to cause the resulting amorphous material to take on various degrees of either hydrophobic or hydrophilic properties. When hydrophobic properties are desired, the methyl or other alkyl substituents are preferred. On the other hand, the amorphous material may be given hydrophilic properties by the use of polar substituents such as $Cl^{\ominus}$ $Me_3N^{\oplus}CH_2CH_2CH_2-$, $HO(CH_2CH_2O)_xCH_2CH_2CH_2-$ or $NH_2CH_2CH_2NHCH_2CH_2CH_2-$.

The present invention includes a method for treating substrates of various types. The method includes the steps of applying solutions of the present invention to the substrate and allowing the volatiles to leave the solution. The volatiles may be allowed to evaporate from the solution under ambient conditions, but they may also be removed by heating, pressure reduction or both.

Such a treatment can be used to give antimicrobial and either hydrophobic or hydrophilic, as desired, properties to substrates. The treatment can be used to protect substrates from attack by fungi normally responsible for mildew, wood-rot, or the like. More typically such substrates are absorbent and include cellulosics, such as wood, cloth and paper, and masonry such as plaster and cinderblock. However, the treatment can also be used to place hydrophobic or hydrophilic antimicrobial coatings on non-absorbent surfaces. Further, this method of treating substrates can be used to improve the hand of natural and synthetic fabrics and to reduce static.

Treating materials by this method has the added advantage that the metal in the siliconate used to treat a substrate will not subsequently leach into the environment by normal weathering, washing or the like. The metal content provides antimicrobial properties while the copolymerically bound silicone resin gives the substrate either hydrophobic or hydrophilic properties, as desired. (However, a metal salt can be added to the solution before drying to achieve controlled leachability, if desired.)

The amorphous material obtained by drying the siliconate solution of this invention is useful as an antimicrobial filler in an ointment. It may be ground, if necessary, to remove any gritty feel before it is mixed with an ointment base. Grinding is typically carried out in a ball mill, although any suitable grinding method may be used. Such a powder can be added to any of the wide variety of well-known ointment bases, such as petroleum jelly, in useful amounts. When the amount of zinc oxide and the amount of the amorphous power of the present invention required to achieve the same antimicrobial effects in an ointment are compared, it is observed that less of the amorphous powder is required. An antimicrobial treatment can be performed on a subject by applying the ointment of the present invention topically to the area to be protected.

The siliconate solution of the present invention can be blended with a variety of water reducible organic materials to achieve either hardening of the organics or plasticizing of the siliconate solutions. A major portion of such an organic and a minor portion of the siliconate solution will improve the hardness of the organic upon reduction. A minor portion of a water reducible organic and a major portion of a siliconate solution of the present invention will improve the film forming properties of the resulting amorphous material when volatiles are removed from the solution. When such a blend is made, the siliconates of the present invention also may contribute their antimicrobial properties to the water reducible material.

Examples of useful water reducible materials are alkyds, acrylic emulsions, hydroxyalkylcellulose, polyvinylalcohols, and mixtures of these materials. The zinc siliconates of this invention can be used with good results in water reducible paints, including zinc oxide-pigmented latex paints.

The following examples further specifically illustrate various representative embodiments of the invention, but are not intended to limit the scope of the invention as defined in the claims.

EXAMPLE 1

An aqueous zinc ammine methylsiliconate solution was prepared by adding 20.0 g. methyltrimethoxysilane to a mixture of 8.14 g. powdered zinc oxide suspended in 50 g. 28% aqueous ammonia in a 4 oz. bottle sealed with a polyethylene cap to withstand slight pressure. The bottle was cooled by shaking under a stream of cold water to remove heat of hydrolysis while the silane reacted and dissolved. The solution was then tumbled until the oxide powder was consumed. No gelation was observed. The oxide was largely consumed in 2 hours, although complete consumption required about 2 days.

This procedure yielded an indefinitely stable solution which had a Si/Zn ratio of 2.2 and a N/Zn ratio of 8.2.

A sample of this solution was air dried on a glass microslide to remove volatiles. The residue was an amorphous, glassy material. Microscopic examination showed this material to be amorphous and examination by X-ray diffraction revealed no indication of crystalline structure. The amorphous material was insoluble in water, alcohol and other common solvent but slowly dissolved in 28% aqueous ammonia with which it reacted to regenerate the ionic zinc ammine methylsiliconate solution.

Siliconate solutions having higher Si/Zn ratios (2.5 to 3.0) were prepared by adding appropriately larger amounts of the silane to the ammoniacal ZnO suspension described above. In such solutions, the zinc oxide dissolved more rapidly than with the lower Si/Zn ratios. With 2.5 and 3.0 Si/Zn ratios, the solutions clarified in less than a day and were also stable indefinitely.

A zinc ammine methylsiliconate solution having an Si/Zn ratio of 3.5 was prepared by the general procedure of this example and was observed to become more viscous, bluish and opalescent within 28 days. The solution gelled in 30–32 days. An analogous solution having an Si/Zn ratio of 4.0 was observed to gel within 18 hours and to become white and stiff on longer standing.

The N/Zn ratio was lowered in solutions having an Si/Zn ratio of 3.0 and 2.5 by using less 28% aqueous $NH_3$ and compensating with $H_2O$. In this way solutions having N/Zn ratios of about 6.6 and about 5 were made, but the rate of ZnO dissolution is slowed by such ratios.

It is seen from this example that stable aqueous metal ammine siliconate solutions can be made at a variety of N/Si/metal ratios. It is seen that ammonia, zinc oxide and methyltrimethoxysilane are useful materials in this invention. Further it is seen that amorphous solids are obtained when volatiles are removed from the solution. It is also evident that these amorphous materials are high molecular weight, insoluble cross-linked copolymeric materials which undergo redissolution only if the ammonia is restored.

EXAMPLE 2

A relatively large laboratory batch of an aqueous zinc ammine methylsiliconate was prepared by adding 327 g. (2.40 moles) methyltrimethoxysilane to a stirred mixture of 600 g. of 28% aqueous ammonia (9.9 moles $NH_3$ in 24.0 moles $H_2O$) and 97.6 g. (1.20 moles) of powdered zinc oxide in a ½ gallon bottle at 15°–20°. The silane was added over a period of 45 min. The bottle was rolled for 5 days when a clear solution was obtained. The solution had a non-volatile solids content of 25.2%, including 9.5% ZnO and 15.7% $CH_3SiO_{3/2}$ which calculates to an Si/Zn ratio of about 2.0 and an N/Zn ratio of about 8.25.

EXAMPLE 3

A clear aqueous silver ammine siliconate solution was prepared by adding 3.0 g. of methyltrimethoxysilane to a mixture of 2.35 g. of powdered silver oxide and 50 g. of 28% aqueous ammonia. After standing 2 weeks in a glass vial either exposed to light or in a darkened cabinet, a silver mirror was obtained on the vial walls. A sample taken from the vial diluted with 4 parts water remained clear and colorless and did not deposit a mirror within a month. Upon applying a portion of this sample to a glass surface and air-drying, the concentrated solids were glassy and brittle and darken with time. It is seen that silver oxide is a useful metal oxide in the present invention.

EXAMPLE 4

Mixed silver-zinc ammine siliconate solutions were formed by dissolving various amounts of powdered silver oxide in solutions similar to that described in the first paragraph of Example 1. In various samples, the $Ag_2O$ content was 0.4%, 2.8% and 18% of the zinc siliconate solids. The air-dried solids were brittle and those incorporating 18% $Ag_2O$ turned brown.

EXAMPLE 5

5.4 g. (0.04 mole) of $MeSi(OMe)_3$ was added in 15 minutes to a mechanically stirred mixture of 3.2 g. (0.040 mole) of cupric oxide powder in 20 g. of 28% aqueous ammonia. A dark gel precipitated around the largely undissolved oxide particles, while the aqueous medium was colored blue. After decanting the blue solution, the residue was stirred with 150 g. of additional 28% aqueous ammonia in portions over a period of 5 days in order to gradually form and to extract soluble salts. Evaporation of the volatiles and drying at 95° gave 2 g. of bluish-white solids. The solids were redissolved in 50 g. of 28% aqueous ammonia. After 16 hours contact, filtrate from a trace of insoluble material was reconcentrated to a bluish-white solid powder which was found by analysis to contain 29.9% copper and 21.0% silicon. The analysis indicated the product to be an amorphous copper methylsiliconate with an Si/Cu ratio of 1.6/1.

It is seen that cupric oxide can be used, albeit with considerable difficulty, in the present invention.

EXAMPLE 6

A deep blue homogeneous solution stable to gelation was obtained by adding with agitation and cooling 7.5 g. of $MeSi(OMe)_3$ to 5.65 g. of a basic cupric carbonate in 50 g. of 28% aqueous ammonia, followed by centrifuging and decantation from a trace of dark copper oxide particles. The cupric carbonate was comprised largely of malachite, a complex salt represented by the formfula $Cu(OH)_2CuCO_3$, having an assay of 56.3% Cu. This gave an overall Si/Cu ratio of 1.1. The silane hydrolyzate reacted with the copper hydroxide moiety to form a cupric ammine methylsiliconate with a Si/Cu ratio of approximately 2.2/1 in a solution which also contained cupric ammine carbonate. Evaporation of the solution gave largely amorphous white solids with a light blue tinge which were water-insoluble and water repellent. In the absence of the basic copper salt, a comparable solution of the silane hydrolyzate in aqueous ammonia set to a hydrogel in 5 minutes. It is seen from this example that basic cupric carbonate is a material which is useful in the invention.

EXAMPLE 7

To a mixture of 1.63 g. of powdered zinc oxide and 13.05 g. of 40% aqueous methylamine (MeNH$_2$), 7.83 g. of MeSi(OMe)$_3$ was added with cooling and shaking. The oxide consumption was gradual and incomplete after 4 days agitation; but gelation of the silane hydrolyzate was prevented. The opaque mixture was centrifuged after 4 days to deposit the unreacted oxide, which, upon washing with water and drying, weighed 0.20 g. The decanted solution was determined by analysis to have a N/Si/Zn molar ratio of 8.4/2.4/1. Upon drying, the solution gave brittle, glassy zinc methylsiliconate solids similar to those from NH$_3$—complexed zinc methylsiliconate. Higher concentrations of the MeNH$_2$ resulted in faster dissolution of the ZnO. It is seen from this example that MeNH$_2$ is a material useful in the present invention.

EXAMPLE 8

To a mixture of 0.81 g. of powdered zinc oxide, 5.05 g. of ethylenediamine and 7.83 g. of water, 3.41 g. of methyltrimethoxysilane was added with cooling and shaking. The oxide dissolved gradually, no gels formed, and the mixture became a hazy solution in 4 hours and a clear solution in 12 hours. The solution was determined to be a zinc ammine methylsiliconate having a N/Si/Zn mole ratio of 8.4/2.5/1.0. Evaporation of volatiles gave hard glassy solids. Similar solutions and solids therefrom were obtained by adding ethylenediamine to the zinc ammine siliconate solution of Example 2 and expelling ammonia by heating to reflux. It is seen from this example that R—NH$_2$ may be ethylenediamine or mixtures of nitrogen-containing compounds, such as ethylenediamine and ammonia. Similar results are obtained when 1,2-propanediamine or other lower alkanediamines are employed instead of ethylenediamine.

EXAMPLE 9

When ammonium carbonate was added to the zinc ammine methylsiliconate described in Example 1 having an N/Si/Zn ratio of 8.2/2.2/1 in amounts such that the carbonate is nearly equivalent to the zinc, the sol which formed gelled within a few minutes. It was observed that with the addition of sufficient material to carbonate 40% of the zinc salt, the ratio of Si/noncarbonated zinc salt is increased to 3.6 and the sol set to a gel in 4 days. With smaller amounts of carbonate, the sols were observed to remain stable with Si/non-carbonated Zn ratios between 2.2 and 3.5.

The deleterious effects of acidic substances in siliconate solutions of the present invention are shown by this example.

EXAMPLE 10

A 42.7 g. batch of the aqueous ammonia-complexed zinc methylsiliconate solution of Example 2, having an N/Si/Zn ratio of 8.2/2.0/1 was concentrated by vacuum drying (25°/10–15 mm.) to remove excess ammonia, methanol and some water to 29.0 g. of a viscous sol, which set overnight to a firm hydrogel. After breaking the gel into small chunks, the vacuum drying treatment was continued until 14.0 g. of hard, glassy solids free of methanol were obtained. The solids were found by analysis to still contain 2.1% ammonia and 22% water. The solids were then redissolved in 5 hours in sufficient 28% aqueous ammonia to give an ammoniacal solution of zinc methylsiliconate in the same weight concentration as in the starting methanol-containing solution. The methanol-free solution then had a N/Si/Zn ratio of 9.45/2.0/1 and was reactive with additional powdered zinc oxide. A 21.35 g. portion of that solution dissolved 1.02 g. of the oxide within 4 days, changing the ratio to 6.45/1.3/1, respectively. Further agitation of that solution that an additional simiilar portion of powdered zinc oxide for 2 days gave partial dissolution. Upon removing unreacted oxide by centrifuging, the zinc oxide enriched solution was found by analysis to contain 14.7% NH$_3$, 15.62% CH$_3$SiO$_{3/2}$ and 17.3% ZnO, indicating a N/Si/Zn ratio of 4.1/1.1/1. It is seen from this example that N/metal ratios approaching the coordination number of the metal are possible and Si/metal ratios of about 1 are possible, even with divalent metals.

EXAMPLE 11

Using the procedure of Example 1, methyltrimethoxysilane was added to several samples 28% aqueous ammonia and zinc oxide powder in amounts sufficient to achieve a 2.2 Si/Zn ratio. It was observed that there was an increase in the rate of ZnO dissolution as the amount of 28% aqueous ammonia was increased. Clear solutions were obtained in less than 20 hours when the amount of aqueous ammonia gave 9.8 to 13.0 N/Zn ratios. When the amount of ammonia was increased to achieve 16.4 N/Zn ratio, zinc oxide dissolution was complete in 2 to 4 hours at 25°.

EXAMPLE 12

Each of several 7.2 g portions of 55% t-butyl alcohol solution of the amidofunctional silane (CH$_3$O)$_3$SiCH$_2$CH$_2$CH$_2$SCH$_2$CH$_2$CONH$_2$ (obtained by reaction of [3-mercaptopropyl]trimethoxysilane with acrylamide) was allowed to hydrolyze with 10.0 g. of 28% aqueous ammonia plus 4.0 g. of ethylene glycol n-butyl ether in the presence of powdered zinc oxide in such amounts that the Si/Zn ratio varied among the several samples from 2.0 to 5.3. Reaction of the oxide was complete in times varying from 3.5 hours to 24 hours as the Si/Zn ratio decreased from 5.3 to 2.0. The solutions obtained were concentrated by evaporation of volatiles to clear tack-free coatings which adhered to glass. Those coatings with 2.7 and 4.0 Si/Zn ratios were quire hard and resistant to fingernail scratching, while a coating with a 5.7 Si/Zn ratio was somewhat pliable and leathery. The primary amido functionality of the organo substituent was shown by infrared and elemental analysis to be retained in the coating and is believed to be responsible, at least in part, for the excellent film-forming properties of this embodiment. It is seen from this example that useful mono-organosilicon materials may be selected to alter the film-forming properties of the solutions.

EXAMPLE 13

(10-carbomethoxydecyl)trimethoxysilane was obtained by the addition of trimethoxysilane to methyl 10-undecylenate containing a trace of chloroplatinic acid. The silane was allowed to react with powdered zinc oxide and aqueous ammonia, as in Example 12, until a homogeneous zinc salt solution is obtained. Infrared and elemental analysis of the devolatilized solids obtained therefrom showed that the 10-carbomethoxydecyl groups were converted predominantly to 10-carbamoyldecyl groups, with a minor part being replaced by zinc ammine decylcarboxylate-containing groupings. When this solution was deposited on a glass surface, air dried and baked at 135°, insoluble, hard, continuous clear coatings were obtained.

EXAMPLE 14

Seventy eight parts of 50% aqueous solution of a hydrolyzate of the silane polyether $(MeO)_3SiCH_2CH_2CH_2SCH_2CH_2CH_2O(CH_2CH_2O)_nH$, where average n equals 12, which silane was obtained by a free radical-catalyzed addition of [3-mercaptopropyl]trimethoxysilane to a polyethylene glycol monallyl ether, was diluted with 100 parts of 28% aqueous ammonia and then allowed to react for 4 hours with 2 parts of powdered zinc oxide. The zinc ammine organosiliconate solution obtained was found capable of being cast as a soft resin film which was amorphous, clear, essentially free of tack and easily wetted with water. The resin solids contain 5.4% zinc oxide by weight, had an Si/Zn ratio of 2 and were more firm than films cast from the zinc-free hydrolyzate.

Compositions with comparable properties were obtained by blending the same starting silane-polyether solution with the zinc ammine methylsiliconate solution of Example 2 in such amounts that the mole ratios of silane polyether to $CH_3SiO_{3/2}$ to ZnO were 1.0/2.0/1.0 and 2.0/2.0/1.0 in two different samples. The cross-linked solids obtained therefrom had ZnO contents of 9.0 and 5.0% respectively. Mixtures of these two solutions and the starting silane-polyether hydrolyzate solutions were found to be useful in modifying the texture of synthetic fabrics. When only small amounts of the zinc siliconates were allowed to dry on the fabric, the hand was soft. With increasing siliconate, the hand was stiffened.

A similarly prepared composition comprising the silanepolyether, $CH_3SiO_{3/2}$ and ZnO units in a mole ratio of 0.5/2.0/1.0, respectively, and a solids weight ratio of 62.4/23.4/14.2, respectively, dried to a clear resin which was comparatively rigid and cracked, yet was water-swellable, picking up 116% of its weight of water with overnight immersion. Hydrophilicity was indicated by the water absorption.

It is seen from examples 12 and 13 that the carbamoyl function in the silicon material aids the film forming properties of the solution of the present invention.

EXAMPLE 15

Zinc ammine vinylsiliconate was prepared in solution (with a N/Si/Zn ratio of 8.2/2.2/1) by the reaction of zinc oxide, suspended in 28% aqueous ammonia, with the silanols formed upon the addition of vinyltrimethoxysilane. Air drying a small portion gave a friable resinous amorphous material which, under the microscope, showed strain patterns, but a lack of crystallinity. The siliconate solids resembled those described in Example 1 and were insoluble.

EXAMPLE 16

In the preparation of aqueous zinc ammine ethylsiliconate solutions with a N/Si/Zn ratio of 8.4/2.2/1 by using ethyltrimethoxysilane for the silane in the procedure of Example 1, reaction of the zinc oxide was comparatively slow (nearly complete after 3 days), yet was sufficiently rapid to block condensation of the silane hydrolyzate to a $(EtSiO_{3/2})_n$ gel. The dried siliconate solid product (31% of the solution, after 1 hour at 150°) was colorless, brittle, amorphous, and insoluble.

EXAMPLE 17

An aqueous solution of a zinc ammine organosiliconate having molar ratios of 8.2 $NH_3$/1.47 $MeSiO_{3/2}$/0.73 $PhSiO_{3/2}$/1.0 ZnO was obtained from the reaction of a 2:1 molar mixture of the silanes $MeSi(OMe)_3$ and $PhSi(OMe)_3$ with zinc oxide in 28% aqueous ammonia. The mixed siliconate dried as an amorphous solid (34% of solution) which was insoluble in water or isopropyl alcohol, but slowly redissolved by reaction with 28% aqueous ammonia.

EXAMPLE 18

A solution of zinc ammine 3,3,3-trifluoropropylsiliconate having N/Si/Zn ratios of 12.3/2.2/1 was readily obtained by a reaction of the silane $CF_3CH_2CH_2Si(OCH_3)_3$ with powdered zinc oxide suspended in 28% aqueous ammonia in 1–3 hours at 25°. The dried resin solids were glassy, brittle (crazed with shrinkage), and hydrophobic.

EXAMPLE 19

A zinc ammine phenylsiliconate was prepared by adding 19.8 g. (0.100 mole) of phenyltrimethoxysilane to a suspension of 4.07 g. (0.050 mole) of zinc oxide powder in 50 g. of 28% aqueous ammonia plus 20 g. of n-butanol. The mixture was shaken with cooling to remove heat from hydrolysis, then tumbled until perfectly clear (in about 8 hours), affording a siliconate salt solution which contained the equivalent of 4.3% zinc oxide and 13.7% $PhSiO_{3/2}$ solids. The solution was stable indefintely and upon air drying gave a highly friable amorphous resin.

EXAMPLE 20

A solution of zinc ammine hexylsiliconate-methylsiliconate with a molar ratio of 0.7 hexyl $SiO_{3/2}$/2.2 $MeSiO_{3/2}$/1.0 ZnO was prepared from a mixture of 0.81 g. of zinc oxide, 1.41 g. of n-hexyltrimethoxysilane, 3.00 g. of methyltrimethoxysilane and 5.0 g. of 28% aqueous ammonia. n-Butanol amounting to 23% of the mixture was added as a common solvent. A clear solution was obtained on overnight tumbling. The same homogeneous product was obtained by adding n-hexyltrimethoxysilane and n-butanol in the same amounts to 8.81 of the solution described in the first paragraph of Example 1, followed by 6 hours of tumbling. Slow evaporation of volatiles from these solutions gave glassy solids which were amorphous, brittle and hydrophobic with a high contact angle for water.

EXAMPLE 21

A solution of a quaternary ammonium salt-containing zinc ammine organosiliconate having a N/Si/Zn ratio of 16.4/1.63/1.00 was prepared by adding 4.2 g. of the quaternary salt $(MeO)_3SiCH_2CH_2CH_2N^{\oplus}Me_3Cl^{\ominus}$ in 3.4 g. of methanol to 10.0 g. of 28% aqueous ammonia containing 0.81 g. of suspended zinc oxide powder. The mixture was shaken, with initial cooling under a water tap, and became a homogeneous solution in less than ½ hour. The solution dried at 25° to a viscous liquid and at 115° (1 to 2 hours) to a solid which was amorphous, brittle and deliquescent, and which reverted to a water soluble liquid under ambient conditions. Blends of the solution product, or the starting quaternary salt-containing organotrimethoxysilane, with larger molar quantities of the zinc ammine methylsiliconate solution of Example 2 provided mixed organosiliconate solutions which dried to solid copolymers which were brittle and insoluble. It was observed that increased concentrations of quaternary ammonium salts produce dried solids which were less hydrophobic than those from the methylsiliconate alone.

The reaction product of 0.81 g. of zinc oxide, 9.91 g. of dimethyl-n-octadecyl [3(trimethoxysilyl)propyl] ammonium chloride, 10.0 g. of 28% aqueous ammonia in 100 g. of 2-n-butoxyethanol, after overnight agitation, was diluted with 15.0 g. of additional 2-n-butoxyethanol and gave a clear, homogeneous solution of a zinc ammine siliconate with an Si/Zn ratio of 2.0/1.0. Upon air drying, the solution gave a non-tacky coating which was firm, soft, water-repellent and water-insoluble, but swollen by toluene.

EXAMPLE 22

A blend of 60 parts of Arolon 363, which is a water thinable soya alkyd resin (50% solids in butoxyethanol and water) and is commercially available from Ashland Chemicals, with 40 parts of the zinc ammine siliconate solution of Example 2 remained homogeneous for 6 hours, becoming hazy overnight and gelling in 2 to 3 days. However, when applied to a surface and dried while homogeneous, this blend dried to a uniform siliconate-modified alkyd coating which was much harder and tougher (when subjected to thumbnail scratching) than that obtained from the alkyd resin alone.

EXAMPLE 23

A 3.56 g. quantity of a flaked silicone resin solid containing $PhSiO_{3/2}$ and $n-PrSiO_{3/2}$ units copolymerized in a 70:30 molar ratio, was dissolved in 10.0 g. of 2-n-butoxyethanol and allowed to react with an agitated mixture of 0.81 g. of powdered zinc oxide in 7.5 g. of 28% aqueous ammonia. A clear solution of the siliconate having an Si/Zn ratio of 3.0 was obtained in 3 hours. A second solution of 3.56 g. of these dry solids in 18.3 g. of 2-n-butoxyethanol was added to several portions of the first solution in various proportions to provide similar zinc ammine organosiliconate solutions with Si/Zn ratios above 3.0. To 3 parts by weight of one of these solutions, with an Si/Zn ratio of 7.7 and in which 0.1% Co and 0.1% Zr were incorporated by addition of the appropriate conventional metal octoate resin driers, was added 1 part of the alkyd resin Arolon 363. The solids present in the resulting silconate-alkyd resin blend contained 37% $PhSiO_{3/2}$, 13% $n-PrSiO_{3/2}$ and 5% ZnO by weight. When the solution blend was applied to a glass surface and allowed to air-dry, it formed a hard coating with good adhesion, clarity and film integrity. When applied as a varnish to aluminum or to a mahogany panel, coatings with good integrity were obtained. It is seen in this example that silicone modified alkyd resins with relatively high Zn concentrations are possible using the zinc ammine siliconate solution of the present invention. It is also shown in this example that even the Si—O—Si bonds of mono-organosiloxanes can constitute useful hydrolyzable substituents in the mono-organosilicon materials when making the siliconate solution according to the present invention. It is further seen that the Si-C bonded substituent may be a phenyl or propyl group, and mixtures thereof.

EXAMPLE 24

An acrylic emulsion (Rohm-Haas Company's Rhoplex® AC-235, 46% in water, often used in latex paints) remained stable for 3 weeks on addition of sufficient solution of Example 2 to give a loading of 20% siliconate solids. This stable emulsion was capable of being diluted with wter. Upon air drying, the zinc siliconate solids appeared to disperse in the coalescing emulsion particles and afforded a uniformly clear coating on glass which is hard and adherent compared with a pliable and readily peeled acrylic control.

EXAMPLE 25

Dilute solutions of the methylsiliconate solution of Example 2 were applied to masonry (concrete and brick) and air dried. The surfaces showed water repellency resembling those treated with a commercially available sodium methylsiliconate control.

EXAMPLE 26

Filter paper (Whatman #1) was immersed in the solution of Example 2 and allowed to air dry to become boardy and parchment-like. No perceptible swelling was observed. After one hour at 75°, the solids weight pickup was 56% based on the weight of the paper. The treated paper was resistant to *Aspergillus niger* fungi in a standard Cosmetics, Toiletries and Fragrances Manufacturers Association (CTFM) 28-day "challenge" test, while a control sample was not.

Subsequent water soaking failed to extract the solids (no weight change was observed) or to alter the stiffness of the paper. However, soaking in 28% aqueous ammonia removed the solids and restored the paper to its original weight and condition. A second filter paper sample was immersed in a similar solution in which 10 wt. % zinc acetate was dissolved. After similar drying, a weight pickup of 77% total solids was observed. Subsequent soaking in water gradually leached out the zinc acetate so that the solids pickup was reduced to 62% in one hour and 57% in three hours.

EXAMPLE 27

An ointment having a petroleum jelly base was formulated with 10% of the powdered methylsiliconate solids of Example 2 ground to a powder with a mortar and pestle. It was highly resistant to *Asperilligus niger* fungi in a standard CTFM 28-day "challenge" test and was much superior in the same test to a similarly formulated ointment containing 10% of powdered zinc oxide instead of the methyl siliconate solids. Another such test indicated the ointment containing solids of Example 2 was resistant to *Pseudomonus aeruginosa* bacteria.

EXAMPLE 28

Methyltrimethoxysilane was added in three 0.50 g. portions with cooling over a period of 1½ hours to a suspension of 0.64 g. of powdered cadmium oxide in 7.67 g. of 28% aqueous ammonia. After agitation overnight, a colorless solution of cadmium ammine methylsiliconate was obtained and had an N/Si/Cd radio of 16.8/2.2/1. Upon standing the solution deposited a small amount of crystals. Upon drying in air, the solution decanted from the crystals gave glassy, amorphous fragments of a material which resembled with zinc siliconate solids of Example 1. A similar solution in which 3,3,3,trifluoromethoxysilane was substituted for methyltrimethoxysilane did not deposit crystals upon standing and upon drying gave an amorphous material such as that of Example 1.

EXAMPLE 29

A mixture of 4.45 g. (0.020 mole) of the silane $NH_2CH_2CH_2NHCH_2CH_2CH_2Si(OMe)_3$, 0.81 g. (0.01 mole) of powdered zinc oxide and 7.00 g. of 28% aqueous ammonia was shaken with cooling under the tap to remove heat of hydrolysis, then tumbled until it became homogeneous (4-20 hours). A similar solution was prepared with a 50% reduction of the 28% aqueous ammonia. In the second solution the ZnO dissolution was much slower (complete in 4-6 days) and the clear solution product was highly viscous, but was thinable with water. When dried on microslides, each solution gave a clear film which embrittled and crazed. The film was initially insoluble but slowly dissolved in water.

EXAMPLE 30

A solution was prepared by adding the aminosilane $NH_2CH_2CH_2NHCH_2CH_2CH_2Si(OMe)_3$ to a methylsiliconate solution in an amount to achieve a N/aminosilane/methylsilane/Zn ratio of 8.3/1.0/2.0/1. The aminosilane went directly into solution. An insoluble opalescent film was obtained when the solution was applied to a glass surface and allowed to evaporate. The film was water wettable, but remained insoluble.

EXAMPLE 31

A mixture of 1.08 g. of red mercuric oxide powder, 10.0 g. of 28% aqueous ammonia, 2.50 g. of ethylene glycol monobutyl ether and 1.20 g. of the silane $CF_3CH_2CH_2Si(OMe)_3$ was shaken for 1 hour. The silane hydrolyzate dissolved in the aqueous phase. A second 1.20 g. portion of the silane was added and agitation was continued for 6 days, with dissolution of most of the oxide and without gel formation. The unreacted oxide was recovered by centrifuging, washing and drying 1 hour in an oven at 150°, where it reverted to 0.29 g. of an orange powder. The solubilized oxide in the colorless solution by difference amounted to 0.69 g. and was present as a mercury ammine siliconate with a Si/Hg ratio of 3.4/1. This solution, upon evaporation and drying 1 hour at 150° afforded colorless, hydrophobic and glassy solids resembling the brittle solids described in Example 18.

EXAMPLE 32

A polyvinyl alcohol (Monsanto Gelvatol having a molecular weight of less than about 2,000) in a 20% aqueous solution was blended with the aqueous solution of Example 2 in a 50/50 solids ratio. A thick homogeneous coating on glass, after air drying and curing 3 hours at 140°, was harder than a PVA coating alone. The dried blend coating showed some shrinkage, but was continuous, coherent and adherent to glass, much in contrast with the solids of Example 2. Thinner coatings obtained from the solution diluted with an equal amount of water were clear, continuous, smooth, hard and tough.

EXAMPLE 33

A zinc ammine methylsiliconate solution with a 2.0 Si/Zn ratio (see Example 2) was added to a 10% aqueous solution of a hydroxypropyl cellulose resin (Hercules "Klucel Type J") to give a 50/50 solids blend in solution. Upon applying the solution to a glass microslide, air drying and curing 3 hours at 135°, a clear, tough coating was obtained. Upon immersing an end of the slide in water overnight, the wet film softened somewhat while maintaining good integrity.

A thicker and foamed sample of the blend solids (0.82 g. after deposition and similar curing in an aluminum dish) showed more softening after a 24 hour water immersion, disintegrated somewhat, and swelled with about 115% water pick-up. In contrast, specimens of the hydroxypropyl cellulose resin alone, similarly deposited and cured as a clear coating or as a translucent disk in an aluminum dish, were comparatively soft, but rigid, before immersion and redissolved in water.

It is seen from this example that water soluble cellulose derivatives such as hydroxyalkyl resins are useful in blends with the solution of the present invention.

The present invention has been disclosed in the above teachings and examples with sufficient clarity and conciseness to enable one skilled in the art to make and use the invention, to know the best mode for carrying out the invention and to distinguish it from other inventions and from what is old. Many variations and obvious adaptations of the inventions will readily come to mind, and these are intended to be contained within the scope of the invention as claimed below.

That which is claimed is:

1. Amorphous materials which are prepared by a method which comprises removing $R$—$NH_2$ and other volatiles from an aqueous metal ammine siliconate solution which is comprised of the reaction products of (a) oxides and hydroxides of metal, metal derivatives or mixtures thereof which are selected from a group consisting essentially of metals of group IB and metals of group IIB of the Periodic Table of Elements, which are not more acidic than the silanols and siloxanols produced in (c), which dissolve in the reaction mixture to yield metal ammine cations in the presence of $R$—$NH_2$;
   (b) $R$—$NH_2$ where R is H, aminoalkyls with 2-6 carbon atoms, or mixtures thereof and wherein the —$NH_2$ molar concentration is equal to at least n times the molar concentration of the metal or metal derivative where n is the coordination number of the metal;
   (c) a mono-organosilicon material which can undergo hydrolysis in the presence of the other reactants to yield mono-organosilanols or siloxanols, and hydrolysis products which are not more acidic than the silanols or siloxanols, wherein the organomoiety in the mono-organosilicon material contains up to about 50 carbon atoms and is selected from the group consisting of saturated and unsaturated hydrocarbons having from 1 to about 6 carbon atoms, halohydrocarbons having up to 6 carbon atoms and wherein the halo substitution is at a location other than the alpha or beta location, aminohydrocarbons, radicals containing one or more ether or thioether linkages, hydroxyfunctional alkyl radicals, carbomethoxyalkyl radicals, carbamoylalkoxy radicals, quaternary ammonium or phosphonium bearing alkyl radicals and mixtures thereof, the mono-organosilicon material being present in an amount sufficient to yield a silicon/metal ratio of from about 1 to about 10; and
   (d) water.

2. Amorphous materials as claimed in claim 1 wherein before the $R$—$NH_2$ and other volatiles are removed, (a) is selected from the group consisting essentially of oxides or hydroxides of zinc, copper, silver, cadmium, mercury, and mixtures thereof.

3. Amorphous materials as claimed in claim 1 wherein before the R—NH$_2$ and other volatiles are removed, (b) is selected from the group consisting essentially of ammonia, methylamine, ethylenediamine, and mixtures thereof.

4. Amorphous materials as claimed in claim 1 wherein before the R—NH$_2$ and other volatiles are removed, (c) is selected from CH$_3$Si(OCH$_3$)$_3$, C$_2$H$_5$Si(OCH$_3$)$_3$, C$_3$H$_7$Si(OCH$_3$)$_3$, CF$_3$CH$_2$CH$_2$Si(OCH$_3$)$_3$, CH$_2$=CHSi(OCH$_3$)$_3$, C$_6$H$_5$Si(OCH$_3$)$_3$, CH$_3$Si(OC$_2$H$_5$)$_3$, C$_2$H$_5$SI(OC$_2$H$_5$)$_3$, C$_3$H$_7$SI(OC$_2$H$_5$)$_3$, CF$_3$CH$_2$CH$_2$Si(OC$_2$H$_5$)$_3$, CH$_2$=CHSi(OC$_2$H$_5$)$_3$, C$_6$H$_5$Si(OC$_2$H$_5$)$_3$ and mixtures thereof.

5. Amorphous materials as claimed in claim 1 wherein before the R—NH$_2$ and other volatiles are removed, (c) contains a polar organofunctional radical.

6. Amorphous materials as claimed in claim 1 wherein before the R—NH$_2$ and other volatiles are removed, (a) is zinc oxide, (b) is ammonia and (c) is methyltrimethoxysilane.

7. Amorphous materials as claimed in claim 1 wherein before the R—NH$_2$ and other volatiles are removed, the ammine siliconate solution also contains at least one material selected from the group consisting essentially of miscible solvents, dyes, colloids, surfactants, soluble metal salts and quaternary ammonium salts.

8. Amorphous materials as claimed in claim 7 wherein the miscible solvent is selected from the group consisting essentially of alcohols, alkoxyalcohols and mixtures thereof, wherein said alcohols and alkoxyalcohols contain up to 6 carbon atoms.

9. Amorphous materials as claimed in claim 7 wherein the added material is selected from polyoxyethylene glycols containing 1 to 15 oxyethylene units, sorbitol, polyvinylalcohols having a molecular weight of less than about 10,000, water soluble cellulosic materials and mixtures thereof.

* * * * *